United States Patent
Prakash et al.

(10) Patent No.: US 7,653,437 B2
(45) Date of Patent: Jan. 26, 2010

(54) METHOD AND APPARATUS FOR DETERMINING OPTIMAL PACING THERAPY TIMING INTERVALS

(75) Inventors: Rajan Prakash, Minneapolis, MN (US); Edward Chinchoy, Golden Valley, MN (US); Thomas J. Mullen, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 657 days.

(21) Appl. No.: 11/344,471

(22) Filed: Jan. 31, 2006

(65) Prior Publication Data

US 2007/0179542 A1 Aug. 2, 2007

(51) Int. Cl.
*A61N 1/368* (2006.01)

(52) U.S. Cl. .................. 607/18; 607/9; 607/25

(58) Field of Classification Search .............. None
See application file for complete search history.

(56) References Cited

U.S. PATENT DOCUMENTS

| | | | |
|---|---|---|---|
| 5,213,098 A | 5/1993 | Bennett et al. | |
| 5,549,650 A | 8/1996 | Bornzin et al. | |
| 6,044,297 A | 3/2000 | Sheldon et al. | |
| 6,070,101 A | 5/2000 | Struble et al. | |
| 6,221,024 B1 | 4/2001 | Miesel | |
| 6,411,848 B2 | 6/2002 | Kramer et al. | |
| 6,738,667 B2 | 5/2004 | Deno et al. | |
| 6,859,665 B2 | 2/2005 | Ding | |
| 6,871,088 B2 * | 3/2005 | Chinchoy | 600/510 |
| 6,882,882 B2 | 4/2005 | Struble et al. | |
| 6,885,889 B2 * | 4/2005 | Chinchoy | 607/9 |
| 2004/0172078 A1 | 9/2004 | Chinchoy | |
| 2004/0186524 A1 * | 9/2004 | Chinchoy | 607/17 |
| 2005/0027320 A1 * | 2/2005 | Nehls et al. | 607/9 |
| 2005/0149137 A1 * | 7/2005 | Chinchoy et al. | 607/25 |
| 2005/0203579 A1 * | 9/2005 | Sowelam et al. | 607/6 |
| 2006/0235289 A1 | 10/2006 | Wesselink et al. | |
| 2008/0269822 A1 * | 10/2008 | Ljungstrom et al. | 607/18 |

FOREIGN PATENT DOCUMENTS

| | | |
|---|---|---|
| WO | WO2004078256 A | 9/2004 |
| WO | WO2005011803 A | 2/2005 |
| WO | WO2005089864 A | 9/2005 |

OTHER PUBLICATIONS

International Search Report, PCT/US2007/060848, May 31, 2007, 7 Pages.

* cited by examiner

*Primary Examiner*—Carl H. Layno
*Assistant Examiner*—Jon-Eric C. Morales
(74) *Attorney, Agent, or Firm*—Reed A. Duthler

(57) ABSTRACT

A method for determining an optimal pacing timing control parameter setting is provided for use in an implantable medical device programmed to deliver a pacing pulse in response to the timing control parameter. The method includes storing a user-selected optimization metric, iteratively adjusting the timing control parameter setting, sensing a first signal that varies in response to left ventricular wall acceleration, measuring the user-selected optimization metric in response to the sensed first signal, and determining an optimal timing control parameter value in response to the measured user-selected optimization metric.

27 Claims, 9 Drawing Sheets

METHOD AND APPARATUS FOR DETERMINING OPTIMAL PACING THERAPY TIMING INTERVALS

TECHNICAL FIELD

The invention relates generally to implantable medical devices, and, more particularly, to an implantable medical device and associated method for selecting timing control parameters for delivering a cardiac pacing therapy.

BACKGROUND

During normal cardiac function, the left ventricle fills during two diastolic phases, a passive filling phase and an active filling phase. The passive filling phase occurs first as the ventricle relaxes following ventricular systole. Ventricular relaxation causes the pressure within the left ventricle to fall, allowing the mitral valve between the left atrium and left ventricle to open. Blood flows into the left ventricle through the left atrium during the passive filling phase due to the pressure difference across the mitral valve. As the passive filling rate slows, the left atrium contracts, actively contributing to ventricular filling. The force generated by the actively contracting left atrium forces more blood into the ventricle.

This atrial contribution to ventricular filling is important in maintaining an adequate preload for optimal ventricular contraction. According to the Frank-Starling law, the ventricles contract more forcefully during systole when filled to a greater degree during diastole. Generally, cardiac stroke volume increases as cardiac filling increases. During many disease states or during various physiologic conditions such as exercise, an overlap between the phases of active atrial contraction and passive left ventricular filling can occur. This can result in reduced atrial contribution to ventricular filling as the pressure gradient across the mitral valve is reversed from normal upon the onset of systole. This contributes to aphysiologic conditions including mitral regurgitation and flow reversal through the pulmonary vein, manifesting itself with a clinical symptom referred to as "pacemaker syndrome". If atrial contraction occurs too late after the passive filling phase, ventricular contraction may have already begun, closing the mitral valve. Thus, late atrial contraction may cause the atria to contract against a closed or partially closed valve, which can result in retrograde flow. Early atrial contraction, prior to the end of the passive filling phase, results in fusion of the passive and active filling phases. The force available from the contracting atria is under-utilized when blood is forced into an empty or only partially filled ventricle. This reduces the overall filling of the left ventricle and results in reduced effectiveness of systolic contraction.

During a number of cardiac stimulation therapies, including dual chamber pacing, cardiac resynchronization therapy, and extra-systolic stimulation among others, an atrial-ventricular (AV) delay is set to control the timing between atrial depolarization and ventricular depolarization. The AV delay can be optimized based on various hemodynamic measurements which are aimed at improving either diastolic or systolic function but may or may not improve both diastolic and systolic function. The AV delay is commonly optimized using echocardiography for maximizing left ventricular filling time while ensuring that the atrial contribution to diastolic filling is not truncated.

A physician's criteria for determining a patient's optimal left AV delay is often based on the patient's underlying disease and symptoms. The patient's symptoms mitigated after an AV delay optimization procedure are therefore dependent on the individual patient's disease, cardiac contractile function or physiologic compensatory mechanisms. The patient's disease and functional state may be associated with systolic or diastolic dysfunction and this information is utilized clinically to determine the various pacing therapy parameters that should be optimized in an attempt to achieve the greatest patient benefit. Furthermore, an AV delay setting determined to be optimal during an office visit may change over time due to changes in disease state, patient activity level, medications or other influences. Other timing parameters, such as AA delays and VV delays may also impact diastolic and systolic function and therefore may be optimized to achieve a desired benefit of a particular pacing therapy. Optimization of one timing parameter may influence the optimal value of another timing parameter.

DETAILED DESCRIPTION

In the following description, references are made to illustrative embodiments for carrying out the invention. It is understood that other embodiments may be utilized without departing from the scope of the invention.

Figure 1A:
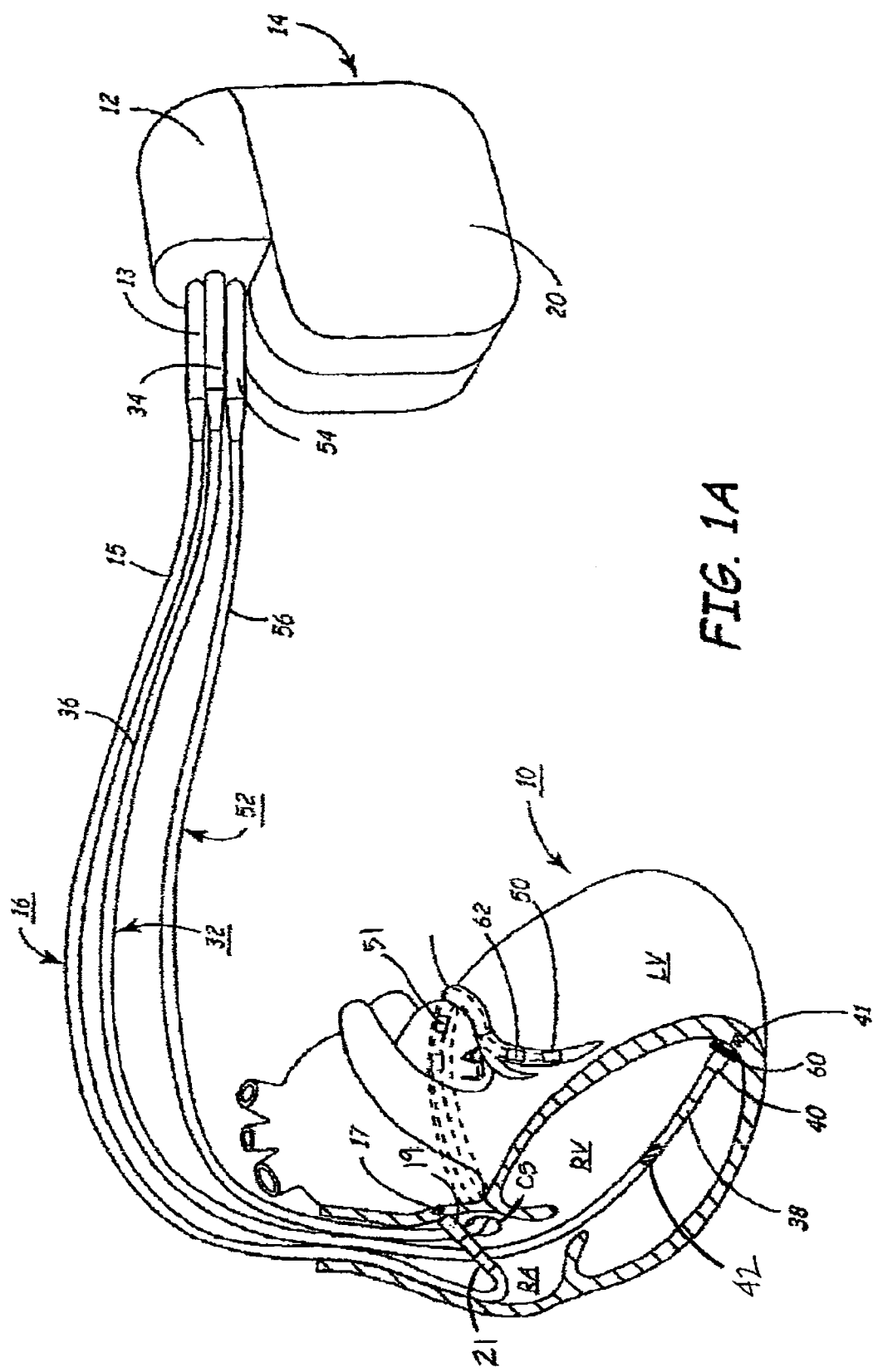
FIG. 1A depicts an implantable, multi-chamber cardiac pacemaker in which one embodiment of the present invention may be implemented.

FIG. 1A depicts an implantable, multi-chamber cardiac pacemaker 14 in which one embodiment of the present invention may be implemented. The multi-chamber pacemaker 14 is provided for sensing intrinsic heart activity and delivering cardiac stimulation pulses as appropriate to one or more heart chambers. Pacemaker 14 may be programmed to operate in any of a number of therapeutic stimulation modes. For example, pacemaker 14 may be configured for delivering cardiac resynchronization stimulation pulses, which control the heart activation sequence for restoring mechanical synchrony within or between one or more heart chambers. Reference is made, for example, to U.S. Pat. Nos. 6,070,101 (Struble, et al.) and 6,871,088 (Chinchoy), both of which patents are incorporated herein by reference in their entirety.

In other embodiments, pacemaker 14 may deliver extra systolic stimulation pulses as needed to achieve post-extra systolic potentiation effects and thereby provide hemodynamic benefit to the patient. Reference is made to U.S. Pat. Nos. 5,213,098 (Bennett et al.), and 6,738,667 (Deno et al.), both of which patents are hereby incorporated herein by reference in their entirety. In various embodiments, pacemaker 14 may be configured to deliver any cardiac stimulation therapy that can be enhanced by or otherwise depends on an optimized AV delay or any other pacing timing control parameters to provide a beneficial effect. Although pacemaker 14 is shown as a multi-chamber pacemaker (sensing and stimulating in three or four heart chambers), it is understood that pacemaker 14 may be modified to operate as a dual chamber pacemaker.

Pacemaker 14 is shown in communication with a patient's heart 10 by way of three leads 16, 32 and 52. The heart 10 is shown in a partially cut-away view illustrating the upper heart chambers, the right atrium (RA) and left atrium (LA), and the lower heart chambers, the right ventricle (RV) and left ventricle (LV), and the coronary sinus (CS) in the right atrium leading into the great cardiac vein 48, which branches to form inferior cardiac veins.

The pacemaker 14, also referred to herein as an "implantable pulse generator" or "IPG," is implanted subcutaneously in a patient's body between the skin and the ribs. Three transvenous endocardial leads 16, 32 and 52 connect the IPG 14 with the RA, the RV and the LV, respectively. Each lead has at least one electrical conductor and pace/sense electrode. A remote indifferent can electrode 20 is formed as part of the outer surface of the housing of the IPG 14. The pace/sense electrodes and the remote indifferent can electrode 20 can be selectively employed to provide a number of unipolar and bipolar pace/sense electrode combinations for pacing and sensing functions.

The depicted bipolar endocardial RA lead 16 is passed through a vein into the RA chamber of the heart 10, and the distal end of the RA lead 16 may be attached to the RA wall using a fixation member 17. The bipolar endocardial RA lead 16 is formed with a connector 13 fitting into a connector bore of IPG connector block 12 that is coupled to a pair of electrically insulated conductors within lead body 15 and connected with distal tip RA pace/sense electrode 19 and proximal ring RA pace/sense electrode 21 provided for achieving RA stimulation and sensing of RA electrogram (EGM) signals.

Bipolar, endocardial RV lead 32 is passed through the RA into the RV where its distal end, carrying tip RV pace/sense electrode 40 and ring RV pace/sense electrode 38, is fixed in place in the RV apex by a distal fixation member 41. The RV lead 32 is formed with a connector 34 fitting into a corresponding connector bore of IPG connector block 12 that is coupled to a pair of electrically insulated conductors within lead body 36 and connected with distal tip RV pace/sense electrode 40 and proximal ring RV pace/sense electrode 38 provided for RV stimulation and sensing of RV EGM signals. RV lead 32 may optionally include a sensor 60 responsive to RV wall acceleration. RV acceleration sensor 60 may be positioned into or proximate the RV apex for detecting acceleration of the RV apical region. In other embodiments, RV acceleration sensor 60 may be disposed at other locations along the RV for sensing RV acceleration.

RV lead 32 may further include a blood pressure sensor 42. Blood pressure sensor 42 may be used for monitoring cardiac function and, in some embodiments, used in combination with either of the right or left wall acceleration signals for optimizing pacing timing control parameters. A RV blood pressure sensor and its use in monitoring cardiac function are generally described in U.S. Pat. No. 6,221,024 (Miesel, Apr. 24, 2001), hereby incorporated herein by reference in its entirety. It is understood that any combination of electrodes and physiological sensors, including, for example, pressure sensors, blood chemistry sensors, flow sensors, acoustical sensors, and impedance sensors, may be included in IPG 14 or an associated lead system. Such sensors may be used in conjunction with an accelerometer for sensing cardiac signals and optimizing cardiac pacing timing control parameters as will be described in greater detail below.

Coronary sinus lead 52 is passed through the RA, into the CS and further into a cardiac vein 48 to extend the distal LV CS pace/sense electrode 50 alongside the LV chamber to achieve LV stimulation and sensing of LV EGM signals. The LV CS lead 52 is coupled at the proximal end connector 54 into a bore of IPG connector block 12. A small diameter lead body 56 is typically selected in order to lodge the distal LV CS pace/sense electrode 50 deeply in a cardiac vein branching from the great cardiac vein 48.

In one embodiment of the invention, coronary sinus lead 52 is provided with a sensor 62 capable of generating a signal proportional to the acceleration of the left ventricular free wall. Sensor 62 may be embodied as a uniaxial, biaxial, or triaxial (or multiaxial) accelerometer contained in a capsule of a relatively small size and diameter such that it may be included in a coronary sinus lead without substantially increasing the lead diameter or impairing the ability to steer the lead to a left ventricular stimulation and sensing site. For the purposes of assessing cardiac function using an accelerometer deployed in operative relation to the left ventricle, a uniaxial accelerometer configured to generate a signal responsive to LV motion substantially along one axis, e.g. longitudinal acceleration, may be sufficient. Radial acceleration might be procured with multiaxial accelerometers to provide more detailed information about LV motion. Sensor 62 may alternatively be provided as another type of transducer such as a transducer having an optical, acoustical, piezoelectric, inductive, capacitive, resistive, or other elements which produce a variable signal proportional to ventricular acceleration or from which variations in ventricular acceleration can be derived.

Sensor 62 is located on CS lead 52 such that when CS lead 52 is positioned for LV stimulation and sensing, sensor 62 is located over the left ventricle and is typically positioned approximately over the left ventricular free wall mid-lateral to mid-basal segments. The depicted positions of the leads and electrodes shown in FIG. 1A in or about the right and left heart chambers are approximate and merely illustrate one of many possible configurations. For example, a left ventricular acceleration sensor 62 may alternatively be located on CS lead 52 such that sensor 62 is positioned along the great cardiac vein, or along any accessible inferior cardiac vein. Furthermore, it is recognized that alternative leads and pace/sense electrodes that are adapted for placement at stimulation or sensing sites on or in or relative to the RA, LA, RV and LV may be used in conjunction with the present invention.

In some embodiments, LV CS lead 52 could bear a proximal LA CS pace/sense electrode 51 positioned along CS lead body 56 such that it is disposed proximate the LA for use in stimulating the LA and/or sensing LA EGM signals. In that case, the lead body 56 would encase an insulated lead conductor extending proximally from the more proximal LA CS pace/sense electrode(s) and terminating at lead connector 54.

Figure 1B:
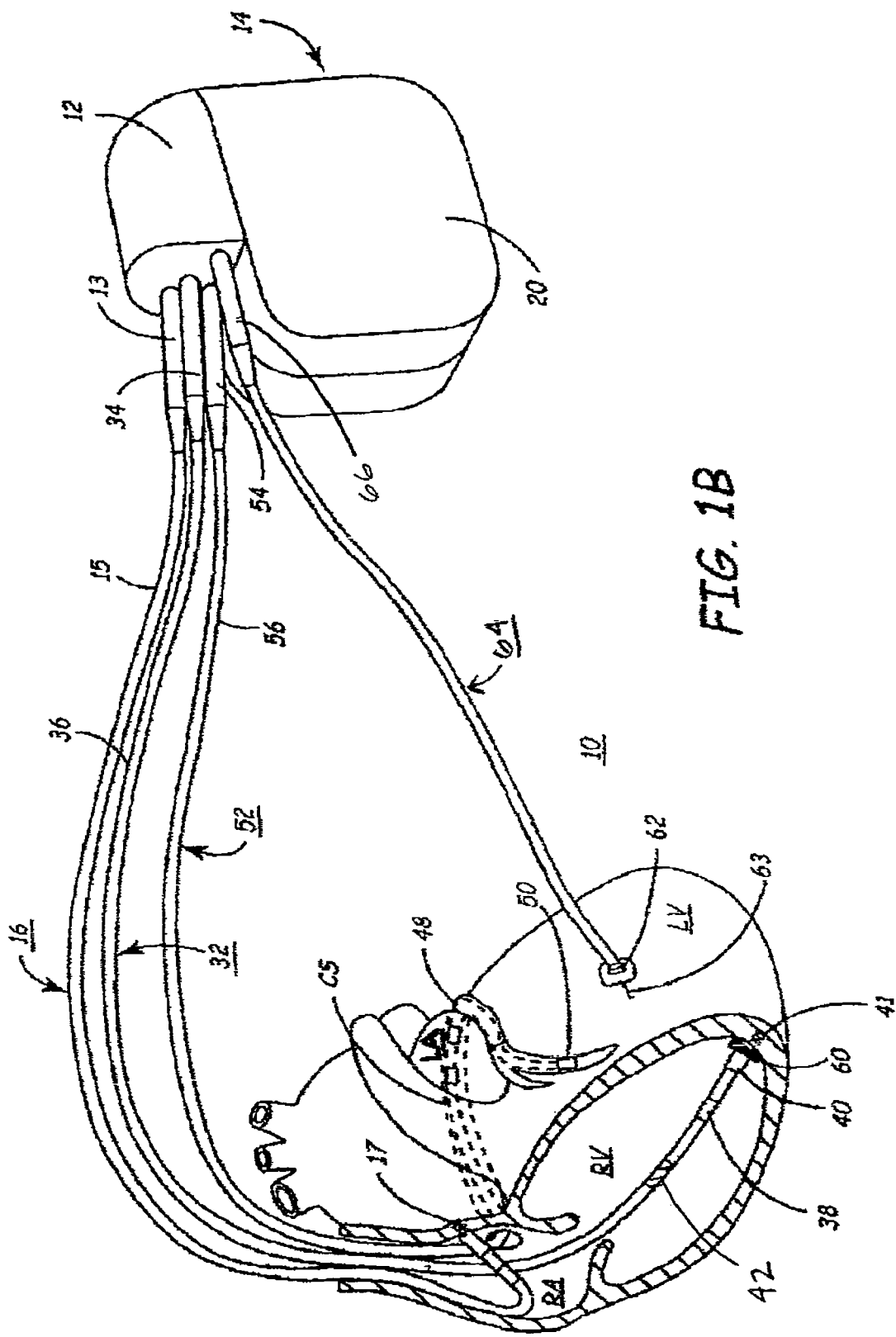
FIG. 1B depicts an implantable, multi-chamber cardiac pacemaker coupled to a patient's heart via transvenous endocardial leads and an additional left ventricular epicardial lead equipped with acceleration sensor.

FIG. 1B depicts an implantable, multi-chamber cardiac pacemaker coupled to a patient's heart via transvenous endocardial leads and an additional left ventricular epicardial lead equipped with acceleration sensor 62. Patients may have previously had a transvenous lead system implanted that includes a coronary sinus lead 52 that is not equipped with an acceleration sensor. Such patients may benefit from the placement of an epicardial lead 64 equipped with an acceleration sensor 62 coupled to IPG 14 via a connector 66 so as to provide an LV acceleration signal.

Epicardial lead 64 is provided with a fixation member 63 which may serve additionally as a pacing and/or sensing electrode. In some cases, an epicardial lead may be preferred over a coronary sinus lead due to the difficulty in advancing a coronary sinus lead into a relatively small cardiac vein over the LV free wall. Placement of a coronary sinus lead can be a cumbersome task due to the tortuosity of the cardiac veins. Therefore, it may be desirable, at least in some patients, to provide an epicardial lead that can be positioned on the LV lateral wall for stimulation, EGM sensing and acceleration sensing, thereby eliminating the need for a coronary sinus lead. Alternatively, it may be desirable to deploy a small diameter coronary sinus lead for LV stimulation and EGM sensing with a separate LV epicardial lead positioned for sensing LV acceleration.

The embodiment generally shown in FIG. 1B may be used for specific selection of cardiac stimulation/sensing sites. With epicardial lead 64 fixed at a desired location for assessing LV acceleration, the effect of pacing at different locations in one or more heart chambers can be evaluated by deploying the transvenous pacing leads 16,32 and 52 to different locations. In particular, coronary sinus lead 52 may be advanced to different locations until an optimal location is identified based on analysis of the signal from LV acceleration sensor 62. By providing acceleration sensor 62 on a separate, epicardial lead 64, the position of LV pace/sense electrode 50, provided on coronary sinus lead 52, may be adjusted independently of sensor 62. If the position of pace/sense electrode 50 needs adjusting, acceleration sensor 62 may remain fixed at a desired measurement site on the LV epicardial wall thereby allowing comparisons to be made between measurements repeated at the same location for different pacing intervals and/or pacing sites.

Any type of transducer may be provided for sensing or deriving ventricular wall acceleration corresponding to the right and/or left ventricle provided such transducers are hermetically sealed, fabricated (at least on the exterior surfaces) of substantially biocompatible materials and appropriately dimensioned for a given application. In addition to transducers that sense acceleration, transducers which sense velocity, displacement or force may be used from which an acceleration component can be derived. With respect to appropriate dimension, a transducer intended for transvenous deployment should be adapted for catheter or over-the-wire delivery. Thus, the radial dimension should generally be on the order of less than about 11 French. The transducer should be somewhat supple with a longitudinal dimension that allows the transducer to safely navigate the venous system, pass through the coronary sinus and enter vessels branching from the coronary sinus. These dimensions are less limited for a transducer intended for deployment though a portion of the chest (e.g., a thoracotomy) with a fixation mechanism adapted to mechanically coupled adjacent the epicardium or pericardium. The dimensions may be relaxed to a greater extent if the epicardial receives the transducer, and to a lesser extent, to a portion of the pericardium. One example of appropriate fixation apparatus for epicardial application is a lead having a distal fixation helix that is screwed into the surface of the epicardium. For pericardial fixation a sealing member (e.g., compressible gasket or opposing members on each side of the pericardial sac) may be used in addition to an active fixation member such as a helical member.

As is also known in the art related to sensors and transducers, accelerometers can be described as two transducers, a primary transducer (typically a single-degree-of-freedom vibrating mass which converts the acceleration into a displacement), and a secondary transducer that converts the displacement (of a seismic mass) into an electrical signal. Most accelerometers use a piezoelectric element as a secondary transducer. Piezoelectric devices, when subjected to a strain, output a voltage proportional to the strain, although piezoelectric elements cannot provide a signal under static (e.g., constant acceleration) conditions. Important characteristics of accelerometers include range of acceleration, frequency response, transverse sensitivity (i.e. sensitivity to motion in the non-active direction), mounting errors, temperature and acoustic noise sensitivity, and mass.

One type of primary transducer, which describes the internal mechanism of the accelerometer, includes a spring-retained seismic mass. In most accelerometers, exerted acceleration forces a damped seismic mass that is restrained by a spring, so that it moves relative to the transducer casing along a single axis. The secondary transducer then responds to the displacement and/or force associated with the seismic mass. The displacement of the mass and the extension of the spring are proportional to the acceleration only when the oscillation is below the natural frequency. Another accelerometer type uses a double-cantilever beam as a primary transducer which can be modeled as a spring-mass-dashpot.

Types of secondary transducers, which describe how the electric signal is generated from mechanical displacement, include: piezoelectric, potentiometric, reluctive, servo, strain gauge, capacitive, vibrating element, etc. These are briefly described as an introduction for the uninitiated.

Piezoelectric transducers are often used in vibration-sensing accelerometers, and sometimes in shock-sensing devices. The piezoelectric crystals (e.g., often quartz or ceramic) produce an electric charge when a force is exerted by the seismic mass under some acceleration. The quartz plates (two or more) are preloaded so that a positive or negative change in the applied force on the crystals results in a change in the electric charge. Although the sensitivity of piezoelectric accelerometers is relatively low compared with other types of accelerometers, they have the highest range (up to 100,000 g's) and frequency response (over 20 kHz).

Potentiometric accelerometers utilize the displacement of the spring-mass system linked mechanically to a wiper arm, which moves along a potentiometer. The system can use gas, viscous, magnetic-fluid, or magnetic damping to minimize acoustic noise caused by contact resistance of the wiper arm. Potentiometric accelerometers typically have a frequency range from zero to 20-60 Hz, depending on the stiffness of the spring, and have a high-level output signal. They also have a lower frequency response than most other accelerometers, usually between 15-30 Hz.

Reluctive accelerometers use an inductance bridge, similar to that of a linear variable differential transducer to produce an output voltage proportional to the movement of the seismic mass. The displacement of the seismic mass in inductance-bridge accelerometers causes the inductances of two coils to vary in opposing directions. The coils act as two arms of an inductance bridge, with resistors as the other two arms. The AC output voltage of the bridge varies with applied acceleration. A demodulator can be used to convert the AC signal to DC. An oscillator can be used to generate the required AC current when a DC power supply is used, as long as the frequency of the AC signal is far greater than that of the frequency of the acceleration.

In servo accelerometers, acceleration causes a seismic mass "pendulum" to move. When motion is detected by a position-sensing device, a signal is produced that acts as the error signal in the closed-loop servo system. After the signal has been demodulated and amplified to remove the steady-state component, the signal is passed through a passive damping network and is applied to a torquing coil located at the axis of rotation of the mass. The torque developed by the torquing coil is proportional to the current applied, and counteracts the torque acting on the seismic mass due to the acceleration, preventing further motion of the mass. Therefore, the current through the torquing coil is proportional to acceleration. This device can also be used to measure angular acceleration as long as the seismic mass is balanced. Servo accelerometers provide high accuracy and a high-level output at a relatively high cost, and can be used for very low measuring ranges (well below 1 g).

Strain gauge accelerometers, often called "piezoresistive" accelerometers, use strain gauges acting as arms of a Wheatstone bridge to convert mechanical strain to a DC output voltage. The gauges are either mounted to the spring, or between the seismic mass and the stationary frame. The strain gauge windings contribute to the spring action and are stressed (i.e., two in tension, two in compression), and a DC output voltage is generated by the four arms of the bridge that is proportional to the applied acceleration.

These accelerometers can be made more sensitive with the use of semiconductor gauges and stiffer springs, yielding higher frequency response and output signal amplitude. Unlike other types of accelerometers, strain gauge accelerometers respond to steady-state accelerations.

In a capacitive accelerometer a change in acceleration causes a change in the space between the moving and fixed electrodes of a capacitive accelerometer. The moving electrode is typically a diaphragm-supported seismic mass or a flexure-supported, disk-shaped seismic mass. The element can act as the capacitor in the LC or RC portion of an oscillator circuit. The resulting output frequency is proportional to the applied acceleration.

In a vibrating element accelerometer, a very small displacement of the seismic mass varies the tension of a tungsten wire in a permanent magnetic field. A current through the wire in the presence of the magnetic field causes the wire to vibrate at its resonant frequency (like a guitar string). The circuitry then outputs a frequency modulation (deviation from a center frequency) that is proportional to the applied acceleration. Although the precision of such a device is high, it is quite sensitive to temperature variations and is relatively expensive.

Figure 2:
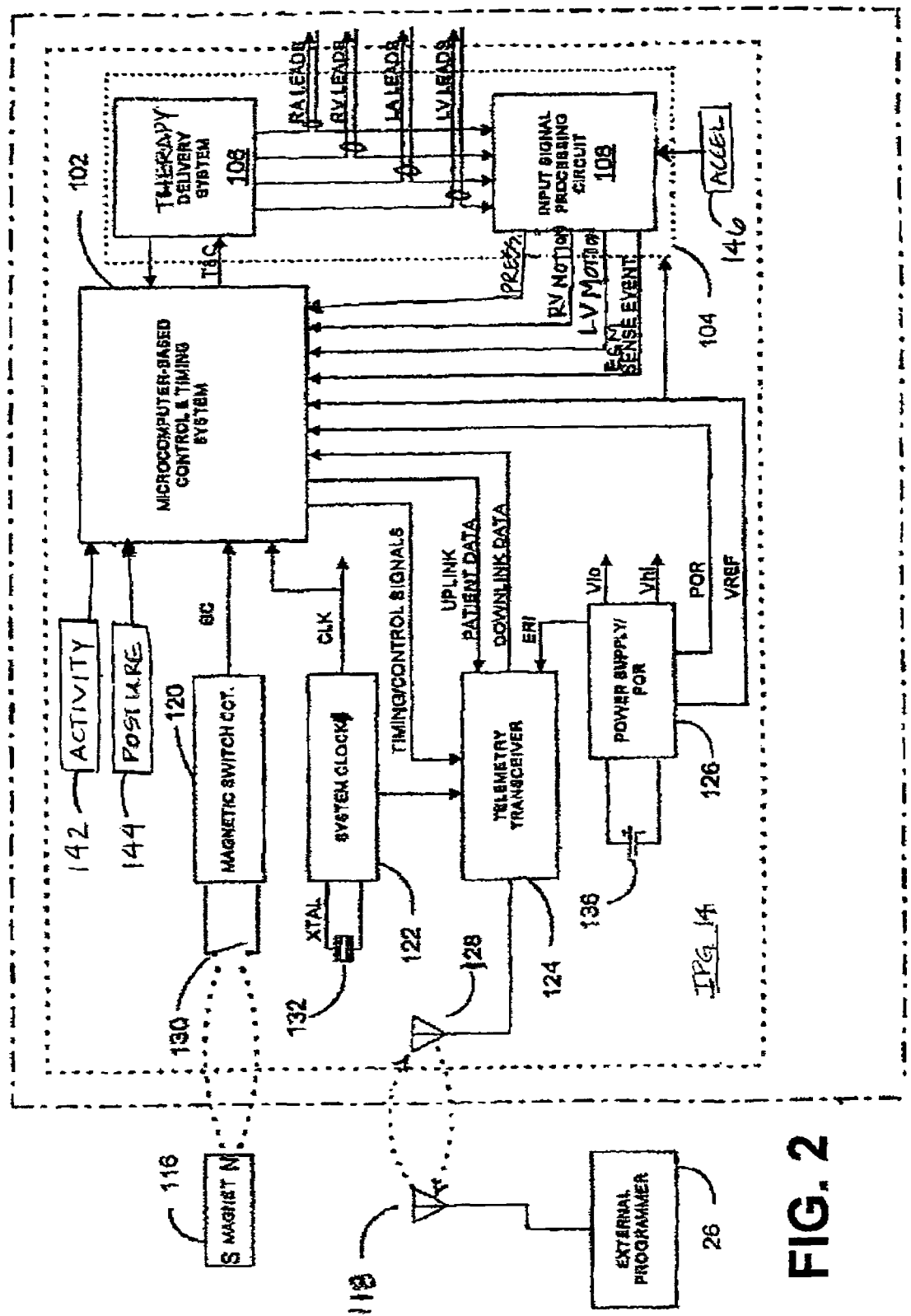
FIG. 2 is a schematic block diagram illustrating one embodiment of a multi-chamber IPG.

FIG. 2 is a schematic block diagram illustrating one embodiment of a multi-chamber IPG 14. IPG 14 is configured to provide a cardiac stimulation therapy and for processing a left ventricular acceleration signal input from any of the types of transducers described above or any other type of transducer sensitive to ventricular acceleration for use in optimizing pacing timing control parameters to achieve an optimized cardiac function metric.

As shown, IPG 14 includes a microprocessor-based control and timing system 102 for controlling the functions of IPG 14 by executing firmware and programmed software algorithms stored in associated RAM and ROM. Control and timing system 102 may also include a watchdog circuit, a DMA controller, a block mover/reader, a CRC calculator, and other specific logic circuitry coupled together by on-chip data bus, address bus, power, clock, and control signal lines in paths or trees in a manner known in the art. It will also be understood that control and timing functions of IPG 14 can be accomplished with dedicated circuit hardware or state machine logic rather than a programmed microcomputer.

The IPG 14 includes interface circuitry 104 for receiving signals from sensors and pace/sense electrodes located at specific sites of the patient's heart chambers and delivering cardiac stimulation aimed at achieving a therapeutic benefit. The interface circuitry 104 therefore includes a therapy delivery system 106 intended for delivering cardiac stimulation pulses under the control of control and timing system 102. Delivery of stimulation pulses in one or more heart chambers is controlled in part by the selection of programmable timing intervals, which can include atrial-atrial (A-A), atrial-ventricular (A-V), and ventricular-ventricular (V-V) intervals and may further include extra systolic intervals or other timing intervals to one or more chambers according to the type of therapy being delivered and the programmed operating mode.

Physiologic input signal processing circuit 108 is provided for receiving cardiac electrogram (EGM) signals for determining a patient's heart rhythm. Physiologic input signal processing circuit 108 additionally receives signals from left ventricular acceleration sensor 62, and RV acceleration sensor 60 and RV pressure sensor 42 when used, processes these signals and provides signal data to control and timing system 102 for further signal analysis. For purposes of illustration, a set of lead connections are depicted for making electrical connections between the therapy delivery system 106 and the input signal processing circuit 108 and sets of pace/sense electrodes, acceleration sensors, and any other physiological sensors located in operative relation to the RA, LA, RV and LV.

Control and timing system 102 controls the delivery of cardiac stimulation pulses at selected timing intervals intended to improve heart function or otherwise alleviate a heart condition as needed. Selection of the programmable intervals includes an analysis of a wall acceleration signal obtained from LV acceleration sensor 62 as will be described in greater detail below. In particular, a ventricular wall acceleration signal is analyzed according to user-selected optimization criteria to optimize pacing timing control parameters, such as AV, AA and VV delays. An AV delay may be controlled by controlling a timed escaped interval following a right atrial or left atrial pacing pulse or sensed depolarization and a subsequent ventricular pacing pulse delivered in either the right or left ventricle. An AA delay may be used to control the relative timing between depolarizations of the right and left atria. Likewise, a VV delay may be used to control the relative timing between depolarizations of the right and left ventricles. The methods described herein for optimizing a pacing timing parameter using a LV accelerometer signal may be applied to any timing parameter used to control the delivery of any pacing therapy.

The therapy delivery system 106 can optionally be configured to include circuitry for delivering cardioversion/defibrillation therapy in addition to cardiac pacing pulses. Accordingly, leads in communication with the patient's heart could additionally include high-voltage cardioversion or defibrillation shock electrodes.

A battery 136 provides a source of electrical energy to power components and circuitry of IPG 14 and provide energy for delivering electrical impulses to the heart. The typical energy source is a high energy density, low voltage battery 136 coupled with a power supply/POR circuit 126 having power-on-reset (POR) capability. The power supply/POR circuit 126 provides one or more low voltage power (Vlo), the POR signal, one or more reference voltage (VREF) sources, current sources, an elective replacement indicator (ERI) signal, and, in the case of a cardioversion/defibrillator capabilities, high voltage power (Vhi) to the therapy delivery system 106. A power supply and interconnections with IPG 14 components may correspond to configurations known in the art.

Electronic IPG circuitry typically employs clocked CMOS digital logic ICs that require a clock signal CLK provided by a piezoelectric crystal 132 and system clock 122 coupled thereto as well as discrete components, e.g., inductors, capacitors, transformers, high voltage protection diodes, and the like that are mounted with the ICs to one or more substrate or printed circuit board. In FIG. 2, each CLK signal generated by system clock 122 is routed to all applicable clocked logic via a clock tree. The system clock 122 provides one or more fixed frequency CLK signal that is independent of the battery voltage over an operating battery voltage range for system timing and control functions and in formatting uplink telemetry signal transmissions in the telemetry I/O circuit 124.

The RAM registers included in microprocessor-based control and timing system 102 may be used for storing data compiled from sensed EGM signals, acceleration signals, and/or relating to device operating history or other sensed physiologic parameters for uplink telemetry transmission upon receipt of a retrieval or interrogation instruction via a downlink telemetry transmission. Criteria for triggering data storage can be programmed via downlinked instructions and parameter values. Physiologic data, including ventricular acceleration data and data derived there from, may be stored on a triggered or periodic basis or by detection logic within the physiologic input signal processing circuit 108. In some cases, the IPG 14 includes a magnetic field sensitive switch 130 that closes in response to a magnetic field, and the closure causes a magnetic switch circuit 120 to issue a switch closed (SC) signal to control and timing system 102 which responds in a magnet mode. For example, the patient may be provided with a magnet 116 that can be applied over the subcutaneously implanted IPG 14 to close switch 130 and prompt the control and timing system to deliver a therapy and/or store physiologic data. Event related data, e.g., the date and time and current pacing parameters, may be stored along with the stored physiologic data for uplink telemetry in a later interrogation session.

Uplink and downlink telemetry capabilities are provided to enable communication with either a remotely located external medical device or a more proximal medical device on or in the patient's body. Stored EGM, or ventricular wall acceleration data as well as real-time generated physiologic data and non-physiologic data can be transmitted by uplink RF telemetry from the IPG 14 to the external programmer or other remote medical device 26 in response to a downlink telemetered interrogation command. As such, an antenna 128 is connected to radio frequency (RF) transceiver circuit 124 for the purposes of uplink/downlink telemetry operations. Telemeteric communication of both analog and digital data between antenna 128 and an external device 26, also equipped with an antenna 118, may be accomplished using numerous types of telemetry systems known in the art for use in implantable devices.

In accordance with one embodiment of the invention, a clinician or other user uses external programmer 26 to program a selected optimization metric for use in an automatic determination of an optimal pacing timing control parameter. As will be described in greater detail below, a user interacting with external programmer may provide programming commands to IPG 14 during downlink telemetry indicating a diastolic, systolic or combination of diastolic and systolic optimization metrics to be used by IPG 14 in executing timing parameter optimization algorithms.

The physiologic input signal processing circuit 108 includes at least one electrical signal amplifier circuit for amplifying, processing and in some cases detecting sense events from characteristics of the electrical sense signal or sensor output signal. The physiologic input signal processing circuit 108 may thus include a plurality of cardiac signal sense channels for sensing and processing cardiac signals from sense electrodes located in relation to a heart chamber. Each such channel typically includes a sense amplifier circuit for detecting specific cardiac events and an EGM amplifier circuit for providing an EGM signal to the control and timing system 102 for sampling, digitizing and storing or transmitting in an uplink transmission. Atrial and ventricular sense amplifiers include signal processing stages for detecting the occurrence of a depolarization associated with a P-wave or R-wave, respectively, and providing an atrial sense or ventricular sense event signal to the control and timing system 102. Timing and control system 102 responds in accordance with its particular operating mode to deliver or modify a stimulation therapy, if appropriate, or to accumulate data for uplink telemetry transmission in a variety of ways known in the art. Thus the need for cardiac stimulation pulse delivery is generally determined based on EGM signal input according to the particular operating mode in effect. However, the intervals at which stimulation pulses are delivered may be determined, at least in part, based on an assessment of ventricular wall acceleration data as will be described below.

As such, input signal processing circuit 108 further includes signal processing circuitry for receiving, amplifying, filtering, averaging, digitizing or otherwise processing the LV wall acceleration sensor signal. Acceleration signal processing circuitry is further provided for detection and/or determination of one or more acceleration signal characteristics such as maximum and minimum peak amplitudes, slopes, integrals, or other time or frequency domain signal characteristics that may be used as metrics of cardiac function. Acceleration data from an LV wall acceleration sensor signal are made available to control and timing system 102 via LV MOTION signal line. LV acceleration data may be used for monitoring cardiac function and is used in algorithms performed for identifying AV timing intervals which meet user-selected optimization criteria. If an RV acceleration sensor is present, an additional RV MOTION signal line provides RV acceleration signal data to control and timing system 102. A PRESSURE signal line provides blood pressure data received from a blood pressure sensor, which may be placed in any of the chambers of the heart or along the circulation system, to control and timing 102.

IPG 14 may further include sensors incorporated in or on the IPG housing. An activity sensor 142 provides a signal to control and timing system 102 responsive to the level of patient activity. A posture sensor 144 provides a signal to control and timing system 102 responsive to the patient's posture. Activity sensor 142 and posture sensor 144 may be used by control and timing system 102 in controlling IPG functions, for example in controlling the delivery of pacing therapies according to a patient's metabolic need and/or posture. According to some embodiments of the invention, activity sensor 142 and posture sensor 144 may be used in verifying stable conditions required for performing timing parameter optimization using an LV acceleration signal. The use of activity sensors in implantable cardiac stimulation devices for determining a level of patient activity and/or providing rate-responsive pacing is known in the art. A posture sensor for use in an implantable medical device is generally described in U.S. Pat. No. 6,044,297 (Sheldon, et al.), hereby incorporated herein by reference in its entirety.

An auxiliary accelerometer 146 may be provided in or on the IPG housing and coupled to input signal processing circuit 108 for use in correcting an LV (or RV) accelerometer signal for noise. Auxiliary accelerometer 146 may be included in an implanted system and positioned at any non-cardiac location to provide a signal that may be used to adjust the LV acceleration signal to remove or minimize the effects of gravity, postural changes, patient activity, or any other non-cardiac acceleration signal sources.

Figure 3:
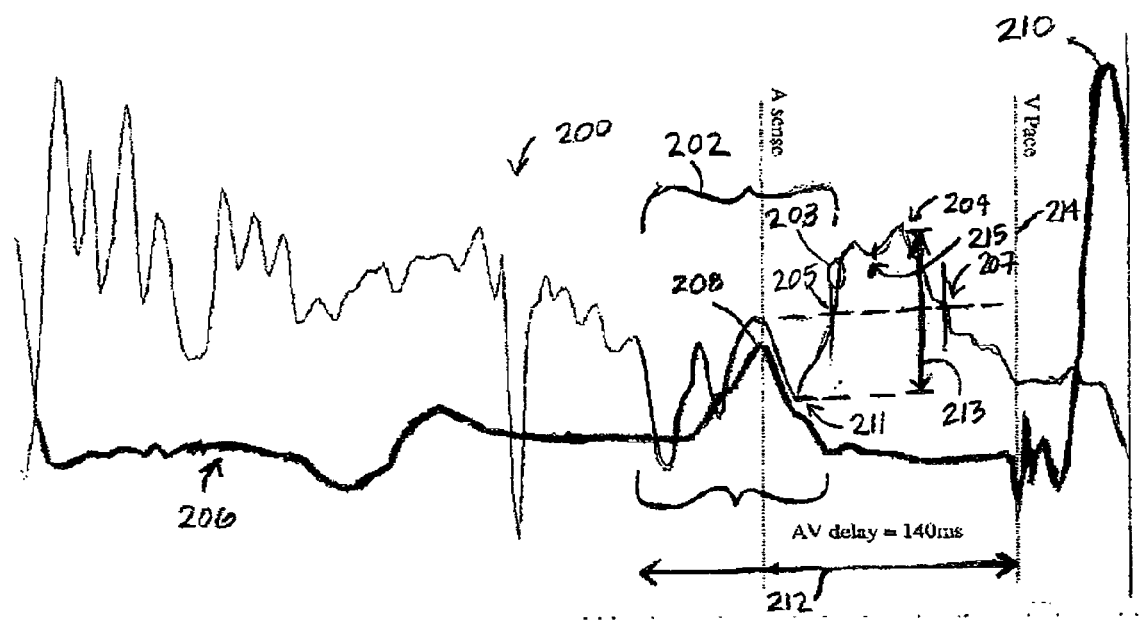
FIG. 3 is a sample LV acceleration signal illustrating diastolic optimization metrics that may be used in determining an optimal pacing timing parameter, such as AV delay.

FIG. 3 is a sample LV acceleration signal. The LV acceleration signal 200 is shown in time with respect to a simultaneously recorded ECG signal 206. During optimal physiologic diastolic coupling, both passive and active filling phases occur without truncation of ventricular filling prior to ventricular contraction. Passive LV filling occurs as the LV myocardium relaxes during a passive filling phase indicated by the bracketed signal 202. At the end of LV relaxation, passive filling slows and the LA contracts, providing active filling of the LV, often referred to as the "atrial kick." During ventricular diastole, the LV acceleration signal 200 thus includes a first filling phase signal 202 associated with LV passive filling. The first filling phase signal 202 is often characterized by alternating positive and negative peaks, morphologically resembling that of a "W". In the example shown, the first filling phase signal 202 is distinguishable from a second filling phase signal peak 204, associated with LV active filling due to atrial contraction. Changes in the timing of atrial contraction alter the relative timing and morphology of the passive filling phase signal 202 and the active filling phase peak 204.

The LV acceleration signal is sensed during a sensing window defined relative to a reliably detectable cardiac cycle event in order to capture the passive and active filling phase signals. For example, diastolic sensing window 212 may be initiated relative to a delivered atrial pacing pulse or a sensed P-wave 208, which can be sensed using an atrial EGM signal, or relative to a ventricular sense or pace event 214. The event used for initiating sensing window 212 may be a right or left heart chamber event. Sensing window 212 may extend until a delivered LV pacing pulse 214 or a sensed R-wave 210 (intrinsic or evoked), which may be sensed using a ventricular EGM signal. The diastolic LV acceleration signal, sensed during diastolic sensing window 212, may be used to derive an optimization metric value representing diastolic function for use in determining an optimal pacing timing control parameter.

In the particular example shown, LV pacing pulse 214 is delivered at a 140 ms AV delay following the sensed P-wave 208. In this case, the 140 ms AV delay results in separation of the passive and active filling phases as indicated by a distinguishable active filling phase signal peak 204 following the passive filling phase signal 202. The LV acceleration signal 200 sensed during diastolic sensing window 212 shown in FIG. 3 illustrates a number of diastolic optimization metrics that may be used for determining an optimal AV delay or other pacing timing control parameter. For example, separation of diastolic filling phases, as indicated by the greatest separation of the two left ventricular filling phases due to passive left ventricular relaxation and left atrial contraction, and a maximized atrial peak acceleration during sensing window 212, may be selected as an optimization metric used in determining an optimal AV delay for diastolic optimization. In other practice, the minimization of time between the two left ventricular filling phases due to left ventricular relaxation and left atrial contraction may be selected as an optimization metric used in determining an optimal AV delay for systolic optimization.

Other optimization metrics that may be derived from the LV acceleration signal include, but are not limited to, the temporal separation of passive filling phase signal 202 from active filling phase peak 204, the time of active atrial filling onset as indicated by threshold crossing 205, an approximate midpoint of diastolic filling (half atrial contraction) as indicated by threshold crossing 207, a maximum slope 203 of LV acceleration signal 200 during sensing window 212, the time of an inflection point 215, a minimum acceleration peak 211, a maximum acceleration peak 204, and a peak-to-peak signal difference 213 or any other signal difference, for example a median-peak difference, mean-peak difference, etc. It is recognized that other metrics useful in optimizing a pacing timing parameter such as AV delay may be derived from the LV acceleration signal 200 during the diastolic phase.

Figure 4:
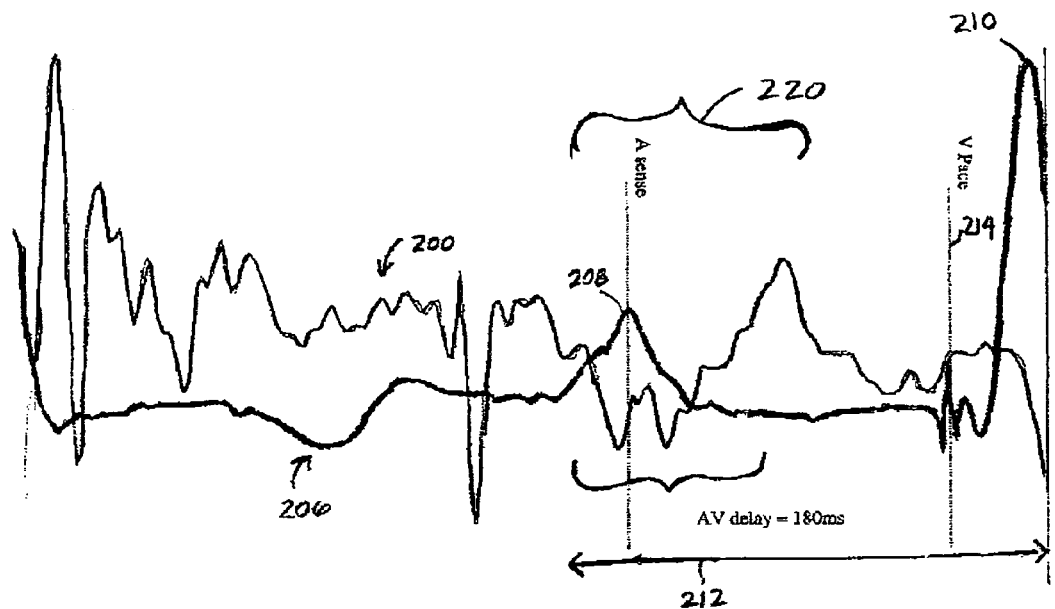
FIG. 4 is a sample LV acceleration signal illustrating fusion of passive and active ventricular filling phases.

FIG. 4 is a sample LV acceleration signal illustrating fusion of ventricular passive and active filling phases. A fused filling phase signal 220 is observed on LV acceleration signal 200 during diastolic sensing window 212. The fused filling phase signal 220 occurs, in this example, when the LV pacing pulse 214 is delivered at a 180 ms AV delay following the sensed P-wave 208. At this longer AV delay, ventricular contraction and ventricular relaxation occur later in the cardiac cycle. As such, the passive filling phase associated with ventricular relaxation occurs later relative to the previous sensed or paced atrial event. The subsequent atrial event, paced or sensed, occurs prior to completion of ventricular relaxation and the passive filling phase. The "atrial kick" that occurs during passive filling to drive blood into an empty or only partially filled ventricle is underutilized. The force of the atrial contraction is better used to drive more blood into the ventricle that has already filled passively.

If the AV delay is too short, the atrium may still be contracting against the build up of pressure generated by the onset of ventricular contraction, which causes the mitral and tricuspid valves to close. As such, the active atrial filling phase will be cut short resulting in incomplete ventricular filling. Incomplete ventricular filling reduces the ventricular stroke volume according to the Frank-Starling law. Under some circumstances, a user may select to optimize the AV delay used during any cardiac stimulation therapy such that the active filling phase associated with atrial contraction occurs after passive filling and prior to the onset of the next ventricular systole to thereby maximize ventricular filling, as shown by the separate passive filling phase signal and active filling phase peak in FIG. 3.

However, in some patients or under some physiological conditions, an AV delay optimized based on a parameter of diastolic function may not be consistent with an AV delay optimized based on a parameter of systolic function. A user may select a systolic optimization metric or a diastolic optimization metric derived from the LV acceleration signal or a combination of both a systolic and diastolic optimization metric for selecting an optimal AV delay or any other pacing timing control parameter in a particular patient or under particular physiological conditions according to a physician's preferences.

Figure 5:
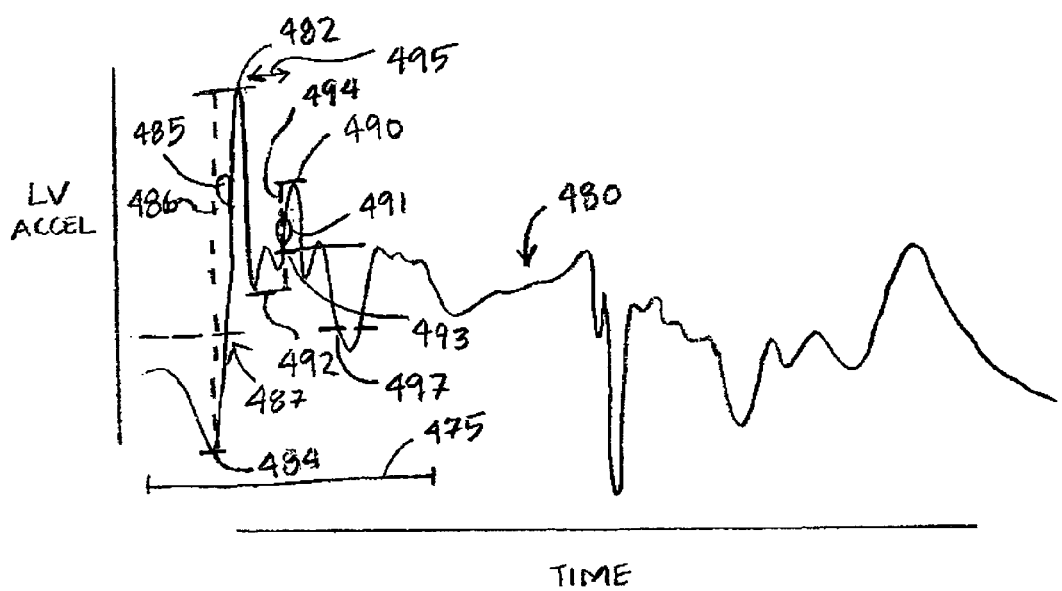
FIG. 5 is an example of an LV acceleration signal illustrating systolic optimization metrics that may be used in determining an optimal pacing timing parameter.

FIG. 5 is an example of an LV acceleration signal illustrating systolic optimization metrics that may be used in determining an optimal pacing timing parameter. A systolic sensing window 475 may be used to enable sensing of the LV acceleration signal 480 during a systolic cardiac phase, in particular during the pre-ejection phase. A first maximum acceleration peak 482 and a second maximum peak 490 typically occur during the pre-ejection phase. The first maximum peak 482 or the first peak-to-peak difference 486 between the first maximum peak 482 and the first minimum peak 484 may be used as a metric of systolic function. The second maximum peak 490 or the second peak-to-peak difference 494 between the second maximum peak 490 and the second minimum peak 492 may be used as a metric of systolic function. Other signal differences may be used other than peak-to-peak signal differences such as peak-to-mean difference, peak-to-median difference, and peak to diastases acceleration.

Other systolic optimization metrics that may be selected for use in optimizing a pacing timing parameter include, but are not limited to: a first minimum peak acceleration 484, a first peak slope 485, the time of an inflection point 492, a second minimum peak 492, the temporal separation 495 of the first maximum peak 482 and the second maximum peak 490, a second maximum slope 491, the onset of pre-ejection acceleration as indicated by a threshold crossing 487, the onset of the second acceleration peak as indicated by threshold crossing 493, an offset of the pre-ejection phase as indicated by threshold crossing 497, or a morphological signature. It is recognized that other systolic function parameters useful in optimizing a pacing timing parameter may be derived from the LV acceleration signal 480. Furthermore, it is recognized that the acceleration signal occurring during systole can have varying morphologies and may sometimes, for example, include a third peak.

Figure 6:
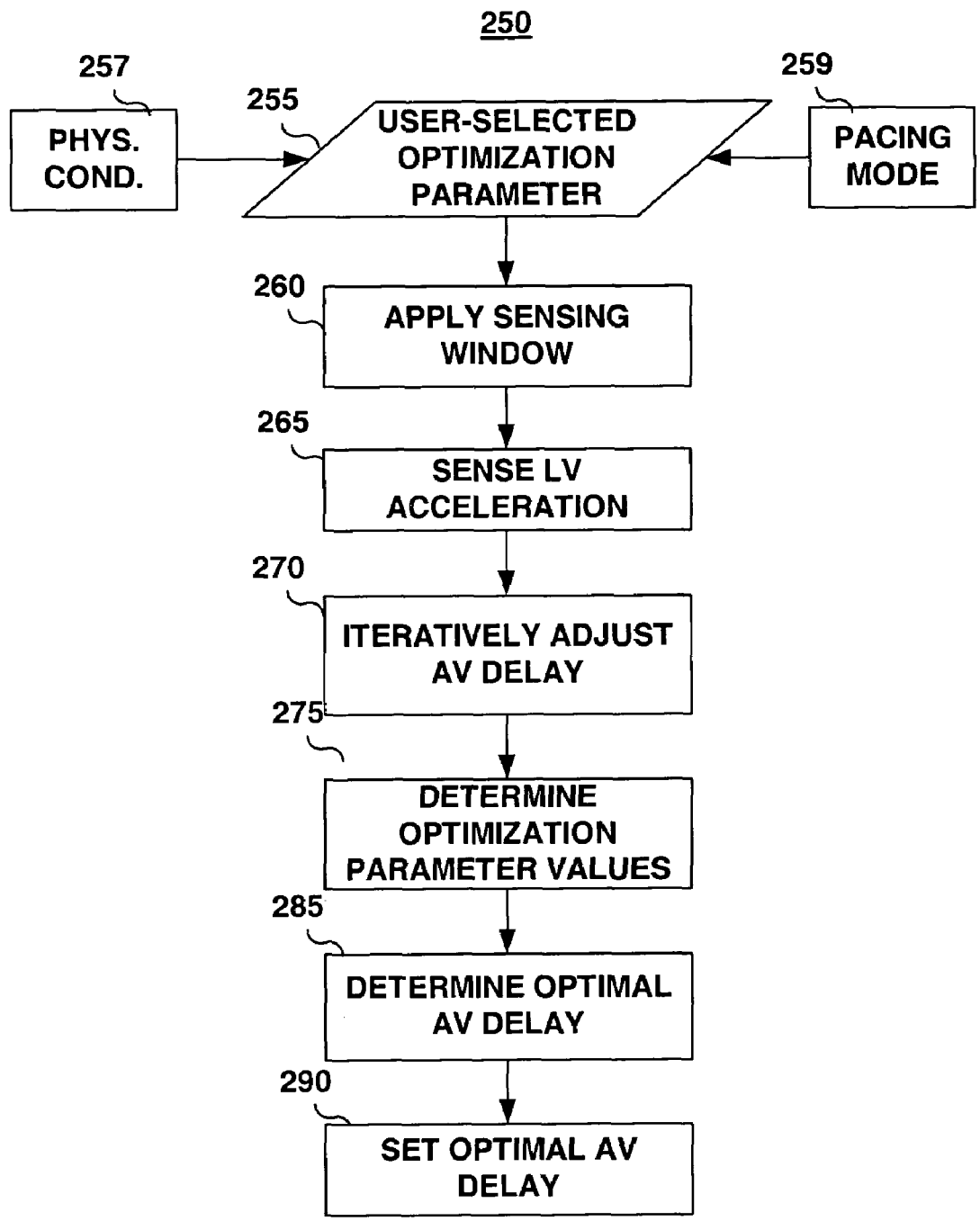
FIG. 6 is a flow chart summarizing steps included in a method for controlling a pacing timing parameter based on LV acceleration signal analysis.

FIG. 6 is a flow chart summarizing steps included in a method for controlling a pacing timing parameter based on LV acceleration signal analysis. The flow chart shown in FIG. 6 and other flow charts presented herein, are intended to illustrate the functional operation of an IPG, and should not be construed as reflective of a specific form of software or hardware necessary to practice the invention. It is believed that the particular form of software/hardware will be determined primarily by the particular system architecture employed in the IPG.

Method 250 refers generally to using an LV acceleration signal for use in optimizing atrial-ventricular coupling. Mechanical coupling between the left atrium and left ventricle can be controlled by adjusting the time delay between an atrial sense or pace event, which may be a right atrial or left atrial sense or pace event depending on the available pace/sense electrodes, and a subsequent ventricular stimulation pulse (in either the right ventricle or left ventricle). However, it is recognized that other timing parameters controlling or influencing inter-atrial electrical coupling, inter-ventricular electrical coupling and atrial-ventricular electrical and/or mechanical coupling can be optimized using the LV acceleration signal for deriving selected optimization metrics.

Beginning at step 255, a user-selected optimization metric is stored for use by method 250. Optimization method 250 uses the user-selected optimization metric in determining an optimal AV delay or other optimal pacing timing parameter. The user may select the optimization metric according to patient need or physician preference. The user-selected optimization metric may be a parameter relating to diastolic or systolic function. Accordingly, the pacing timing parameter will be optimized based on the selected function.

As indicated by block 259, storing the user-selected optimization metric may include storing for which pacing mode(s) the optimization metric should be applied. In a device capable of operating in multiple pacing modes, a user may select different optimization metrics for use in optimizing timing intervals used by the different pacing modes. For example, the user may specify one optimization metric to be used in optimizing AV delay during cardiac resynchronization therapy and may specify a different optimization metric to be used in optimizing the AV delay during a dual chamber pacing mode or a rate-responsive pacing mode. As such, step 255 may include storing user-selected optimization metrics as well as the pacing modality to which the selected optimization metric applies. Pacing modalities may include, but are not limited to, dual-chamber pacing, rate-responsive pacing, multi-chamber pacing, bi-ventricular pacing, fusion pacing, minimized ventricular pacing, cardiac resynchronization therapy, extra systolic stimulation therapy, and arrhythmia prevention therapies.

Additionally or alternatively, the user may specify a physiologic condition for which the user-selected optimization metric should be applied as indicated by block 257. For example, the user may specify one optimization metric to be used at rest and different optimization metric to be used during exercise. A determination of a resting state and an exercising state may be made by the device according to programmed or predefined threshold criteria using any available sensor signals, such as an activity sensor, posture sensor, and/or heart rate. In another example, the user may specify one optimization metric to be used during a substantially prone position and another optimization metric for use during a substantially upright position as determined by a posture sensor. In other embodiments, optimization metrics may be selected by a user and stored according to heart rate ranges, blood pressure ranges or any other physiological condition monitored by the implanted device.

Optimization metrics that may be selected for maximizing diastolic function are described above in conjunction with FIGS. 3 and 4 and include, but are not limited to, detection of separate passive and active filling peaks, maximum temporal separation of passive and active filling peaks, an acceleration signal peak, a peak-to-peak difference or other signal change metric such as a median-to-peak difference, a mean-to-peak difference, or peak of diastases acceleration, a slope, an integral, an inflection point, or a morphological signature determined from the LV acceleration signal during a diastolic phase of the cardiac cycle.

Alternatively the optimization metric may be selected as a metric that is indicative of systolic function for maximizing hemodynamic function. Optimization metrics that may be selected for maximizing systolic function are described above in conjunction with FIG. 5 and include a peak acceleration signal, peak-to-peak acceleration signal difference or other signal difference as listed above, an integral, slope, inflection point, or morphological signature or other characteristic of the LV acceleration signal during a systolic portion of the cardiac cycle.

An appropriate sensing window is applied at step 260. The sensing window applied at step 260 corresponds to the user-selected optimization metric stored at step 255. For example, if a diastolic optimization metric is selected, a diastolic sensing window 212 is applied as illustrated in FIGS. 3 and 4. If a systolic optimization metric is selected, a systolic sensing window 218 is applied, also illustrated in FIGS. 3 and 4. The LV acceleration signal is sensed at step 265 from an accelerometer or other appropriate transducer deployed along the LV, typically along the LV free wall.

In one embodiment, the sensing window is initiated upon an EGM sensed event, which may be a depolarization sensed in any pre-determined heart chamber, or a paced event. In other embodiments, the LV acceleration signal may be sensed over the entire cardiac cycle and the sensing window for timing parameter optimization may be set relative to a feature of the LV acceleration signal. For example, the sensing window may be set relative to an LV acceleration peak or any other reference point that can be reliably detected on the acceleration signal. Alternatively, the sensing window could be set relative to other sensed signals which contain cardiac cycle information including blood pressure signals. The sensing window may be set using one or more sensed signals; the sensing window start time may be set using one sensed signal and the sensing window end time may be set using a different sensed signal. For example, the start time may be set using an EGM sensed event or a paced event and the end time may be set using a fiducial point detected on the acceleration signal. It is recognized that a sensing window may be defined according to different sensed signals and different characteristics of those sensed signals. Furthermore, the sensing window applied at step 260 may be defined uniquely according to the user-selected optimization metric stored at step 255.

At step 270, a pacing timing parameter is adjusted to a number of settings. The timing parameter may be iteratively adjusted in an increasing, decreasing, random, or other search pattern, such as a binary search pattern. The initial setting may be a nominally selected setting or a previously determined optimal setting. At each setting, the LV acceleration signal is analyzed at step 275 to determine the value of the selected optimization metric for the corresponding timing parameter setting.

At step 285, the optimal value for the timing parameter is determined based on the determined optimization metric values. Generally, the optimal timing parameter value corresponds to the setting at which the optimization metric is maximized, however, depending on the particular optimization metric selected, an optimal timing parameter value may correspond to a minimized optimization metric or other optimization metric criteria. At step 290, the timing parameter may be automatically programmed to the optimal value determined at step 285. Methods for optimizing AV delay using a LV acceleration signal based on diastolic function are generally disclosed in co-pending U.S. patent application Ser. No. 11/245,623, hereby incorporated herein by reference in its entirety. Methods for selecting cardiac therapy settings that correspond to a maximum LV acceleration during isovolumic contraction are generally disclosed in U.S. Pat. No. 6,885,889 (Chinchoy), hereby incorporated herein by reference in its entirety.

Steps 260 through 265 of method 250 may be repeated periodically or upon a detected change in heart rate, activity, pacing mode, or other triggering event to re-determine the optimal pacing timing parameter during changing conditions. A user may change the optimization metric at step 255 at any time. Furthermore, it is recognized that method 250 may be performed for optimizing a first timing parameter while other timing parameters remain fixed at previously determined optimal parameter settings or at nominal settings. Method 250 may then be repeated for optimizing a second timing parameter while the first timing parameter remains at the newly determined optimal value. Alternatively, block 270 may include iteratively adjusting a combination of timing parameters, for example iteratively adjusting combinations of AV delay and VV delay settings. The optimization metric values determined at block 275 will be indicative of the diastolic or systolic function during application of the varying combinations of two or more timing parameters.

Figure 7:
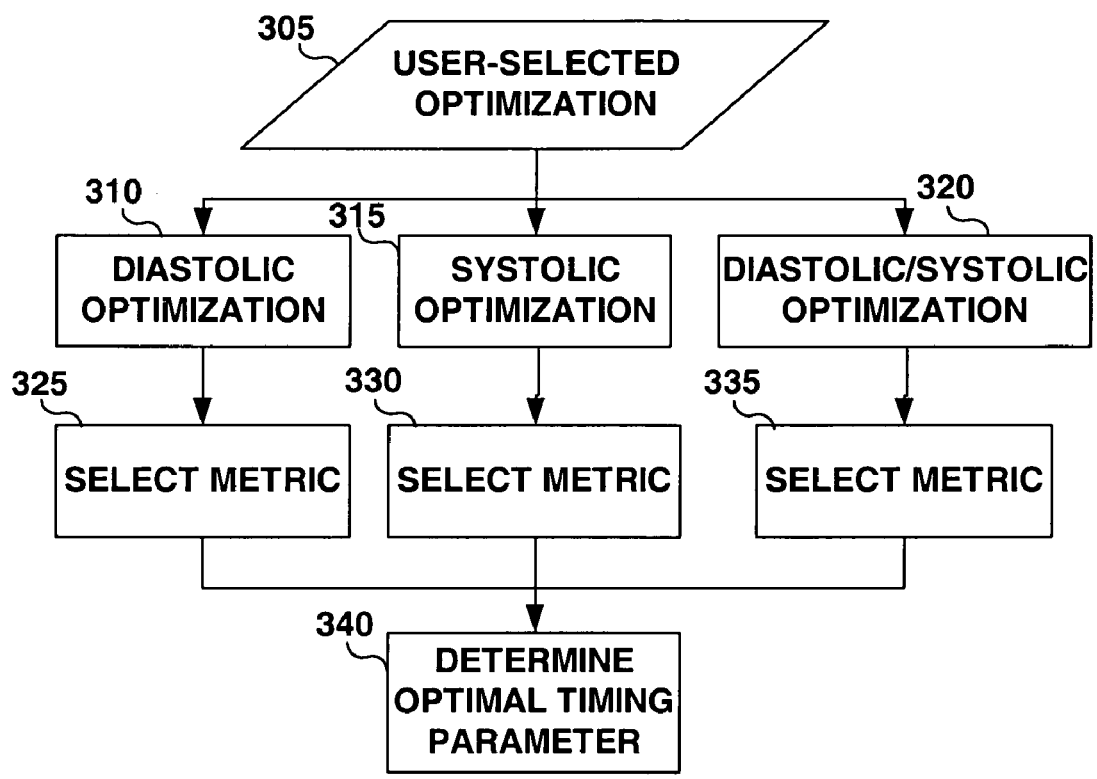
FIG. 7 is a block diagram summarizing a hierarchy of user-selectable optimization metrics.

FIG. 7 is a block diagram summarizing a hierarchy of user-selectable optimization metrics. At block 305, method 300 waits for user-provided input indicating a selected optimization metric. In some embodiments, a user may select diastolic optimization 310, systolic optimization 315, or a combination of diastolic and systolic optimization 320. Based on the selection of diastolic optimization, systolic optimization, or combination thereof, the timing parameter optimization is performed at block 340. The timing parameter optimization, as summarized in FIG. 6, is performed based on a nominal optimization metric corresponding to the diastolic, systolic, or combined diastolic/systolic optimization mode selected by the user.

For example, if diastolic optimization is selected at block 310, the timing parameter optimization method performed at block 340 may automatically set a sensing window corresponding to a diastolic phase and determine a nominal diastolic function metric, such as separation of LV acceleration peaks corresponding to active and passive filling, for use in determining an optimal timing parameter such as AV delay. If systolic optimization is selected at block 315, the optimization method performed at block 340 may automatically set a sensing window corresponding to a systolic phase and determine a nominal systolic function metric, such as maximum peak LV acceleration, for determining an optimal timing parameter. Likewise, if a combination of diastolic and systolic optimization is selected at block 320, the optimization method 340 automatically sets diastolic and systolic sensing windows for determining nominal diastolic and systolic optimization metrics for use in determining an optimal timing parameter.

Thus, in some embodiments, a user may select a specific optimization metric. In other embodiments, a user may select whether the timing parameter should be optimized based on diastolic function, systolic function or a combination of both. The IPG then uses predetermined nominal metrics corresponding to the selected optimization mode during the timing parameter optimization procedure.

In other embodiments, the user may select diastolic, systolic or a combination of diastolic/systolic optimization and make a further selection, at one of blocks 325, 330 and 335, of the particular optimization metric to be used. For example, if a user selects diastolic optimization at block 310, the user may go on to select a particular diastolic optimization metric at block 325. The timing parameter optimization performed at block 340 then sets a sensing window in accordance with the selected diastolic optimization metric and determines the optimal timing parameter value corresponding to the selected metric.

If a user selects systolic optimization at block 315, the user may select a particular systolic optimization metric at block 330. The optimization method performed at block 340 then sets a sensing window in accordance with the selected systolic optimization metric and determines the optimal timing parameter value corresponding to the selected parameter.

Likewise, if a user selects a combination of diastolic/systolic optimization at block 320, the user may select a particular diastolic optimization metric and a particular systolic optimization metric at block 335. The optimization method performed at block 340 then sets sensing windows accordingly and determines an optimal timing parameter value based on the selected optimization metrics.

Figure 8:
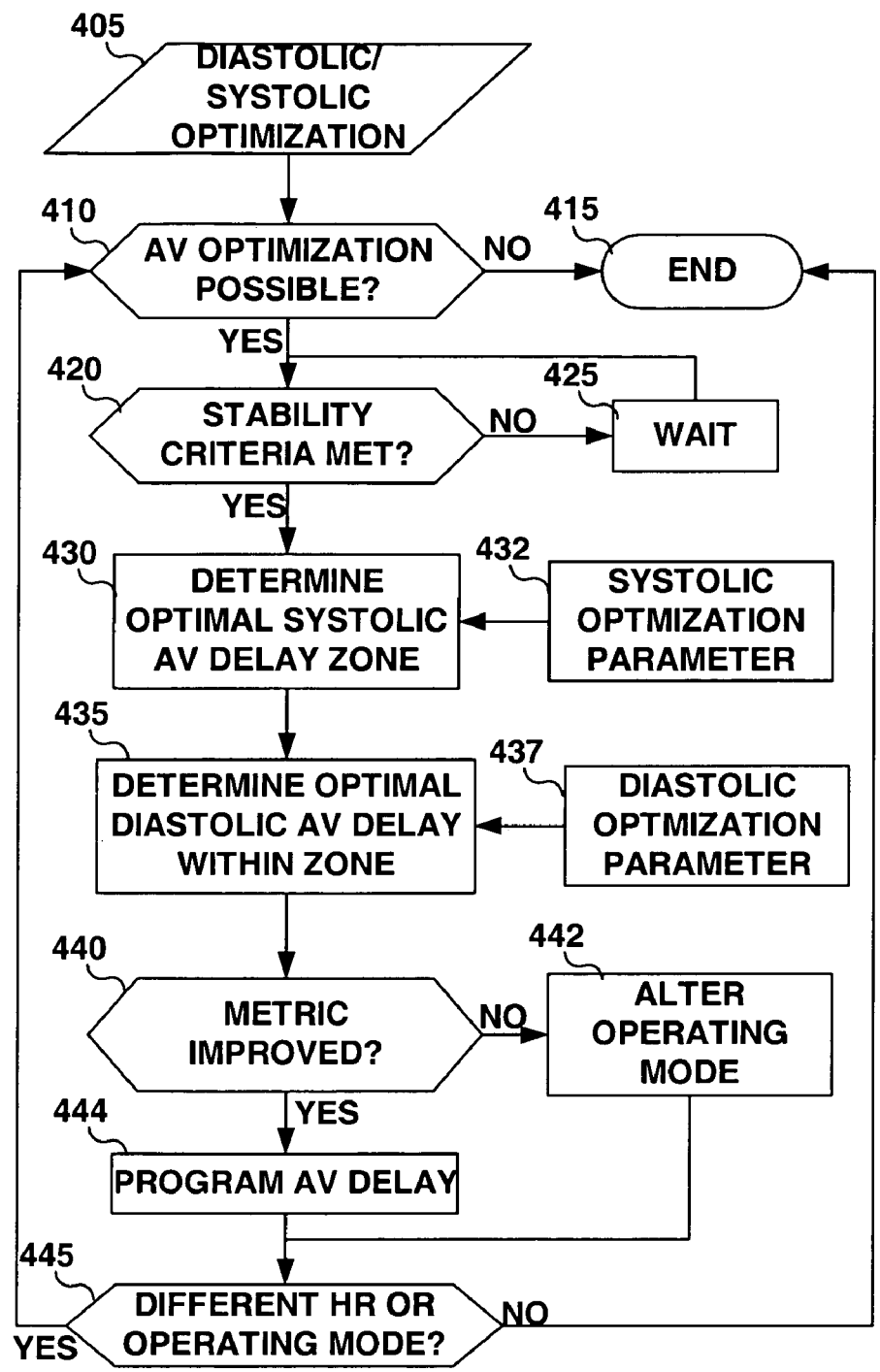
FIG. 8 is a flow chart summarizing steps performed in a method for optimizing AV delay based on a combination of systolic and diastolic function.

FIG. 8 is a flow chart summarizing steps performed in a method for optimizing AV delay based on a combination of systolic and diastolic function. When a combination of diastolic and systolic optimization metrics are selected, the AV delay optimization method may include performing an AV delay optimization based on one optimization metric to narrow the range of the AV delay settings. An optimal AV delay value is then determined within the narrowed range of optimal settings based on the second optimization metric. While method 400 shown in FIG. 8 is described with regard to optimization of an AV delay, it is recognized that method 400 may be applied to any pacing timing control parameter. The steps carried out in performing method 400 are therefore not limited to AV delay optimization procedures but may also be applied to AA delay, VV delay or any other timing parameter optimization procedures.

At step 405, method 400 receives input that a combined diastolic and systolic optimization of AV delay should be performed. In some embodiments, the diastolic/systolic optimization selection may be a nominal selection pre-programmed into the IPG. Alternatively, a user may select the diastolic/systolic optimization. At step 410, the IPG determines if AV delay optimization is possible. Atrial fibrillation, atrial tachycardia or other confounding physiologic or pathophysiologic conditions may be present preventing application of an optimized AV delay in some patients. AV delay may not be a control parameter in use by the IPG depending on the operating mode or type of therapy being delivered. As such, AV delay optimization may not be feasible in all patients at all times. If AV delay optimization is not possible, method 400 is terminated at step 415 any may be reinitiated automatically or manually at a later time.

If AV delay optimization is determined to be possible at step 410, method 400 verifies that stability criteria required for performing AV delay optimization are met at decision step 420. The IPG may execute the AV delay optimization procedures during stable heart rate, stable pacing mode, and/or stable patient activity level to promote reliable AV optimization results. As such, the IPG may verify that the heart rate varies within an acceptable heart rate range at decision step 420. Heart rate data may be obtained from EGM signals sensed by the IPG as described previously. The IPG may additionally or alternatively verify that the patient activity level remains within an acceptable range at decision step 420. The AV delay optimization procedure may be performed when the heart rate and/or activity level correspond to a resting condition. Alternatively, AV delay optimization procedures may be performed at different heart rates and/or activity levels as long as the heart rate and/or activity level remains within a predetermined range throughout the optimization procedure.

In some embodiments, other sensors may be used in addition to or alternatively to an activity sensor for verifying stable conditions for performing AV delay optimization. For example, stable patient activity or condition may be verified using a posture sensor or respiration rate detection using an impedance sensor or the accelerometer sensor signal. Gravitational effects on the acceleration signal may be minimized by requiring that the patient's postural position, as indicated by a posture sensor, remains stable throughout the AV delay optimization procedure. Respiratory contributions to the accelerometer signal may be controlled by verifying a stable respiration rate. Stability criteria may include a time of day requirement. For example, AV delay optimization may be performed during night time hours when the patient is expected to be asleep and having a stable heart rate, activity, and posture.

If stability criteria are not met at step 420, method 400 waits at step 423 and monitors the relevant signals (e.g., heart rate, activity, posture, time of day) until the stability criteria for performing AV delay optimization are met. Additionally or alternatively, the LV acceleration signal may be corrected at step 425 to remove or minimize non-cardiac contributions to the acceleration signal. For example, gravitational effects on acceleration data may be removed or minimized by normalizing the acceleration signal metrics by a mean or median acceleration signal magnitude or any other indexing factor that may be derived from the LV acceleration signal. In other embodiments, signal averaging over a number of cardiac cycles, filtering, or other signal processing methods may be used to correct the LV acceleration signal for non-cardiac signal contributions.

In some embodiments, a signal acquired from an auxiliary accelerometer, placed in a non-cardiac location, may be used for correcting the LV accelerometer signal for noise due to postural changes, activity, respiration, or other non-cardiac body motion. For example, a signal obtained from an auxiliary accelerometer incorporated in the IPG housing may be subtracted from the signal obtained from the accelerometer implanted along the left ventricle.

At step 430, an optimal AV delay zone is determined based on a systolic optimization metric provided as input to the systolic optimization method 430 at block 432. The systolic optimization metric may be a user-selected metric or may be a nominal metric used by the IPG to determine an AV delay associated with optimal systolic function.

Figure 9:
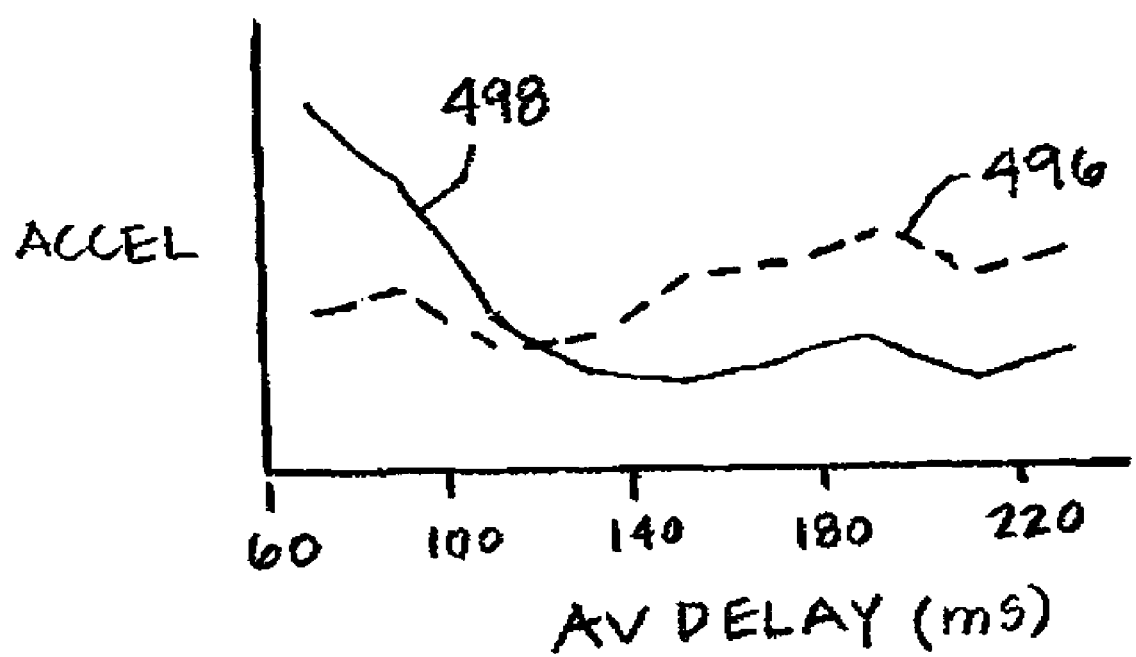
FIG. 9 is a graph of the pre-ejection peak-to-peak acceleration differences measured during pacing at different AV delays.

FIG. 9 is a graph of the first peak-to-peak difference and second peak-to-peak difference measured during the pre-ejection phase while pacing at different AV delays. The first peak-to-peak difference 496 is plotted in dashed line. The second peak-to-peak difference 498 is plotted in solid line. An optimal AV delay zone may be defined based on a systolic LV acceleration metric such the first or second peak-to-peak differences shown in FIG. 5. For example, maximum acceleration of the LV during the pre-ejection phase occurs at AV delays less than about 120 ms. Referring again to the optimization method 400 shown in FIG. 8 and with regard to the example data shown in FIG. 9, an optimal AV delay range between 60 and 120 ms may be determined at step 430 based on the systolic optimization metric of second peak-to-peak difference.

Once an optimal AV delay range is identified, the AV delay may be further optimized using a diastolic optimization metric at step 435. The diastolic optimization metric, received as input to the diastolic optimization method 435 at block 437, may be a nominal metric used by the IPG or a user-selected metric. Diastolic optimization of the AV delay performed at step 435 may correspond generally to the optimization methods disclosed in above-incorporated U.S. patent application Ser. No. 11/245,623 (Prakash, et al.). Diastolic AV delay optimization is performed at step 435 by varying the AV delay settings over the optimal AV delay zone determined based on the systolic optimization metric at step 430. The optimal AV delay value determined based on the diastolic optimization metric at step 435.

When AV delay is optimized according to both a diastolic metric and a systolic metric of cardiac function, one of the optimization metrics used may be derived from a sensor signal other than the LV acceleration signal. For example, a user may select to optimize diastolic function based on the LV acceleration signal and systolic function based on a blood pressure signal. For example, the optimization may be based on maximizing systolic dP/dt determined from a pressure sensor signal while maintaining physiologic diastolic coupling as evidenced by separation of the passive and active filling peaks on the LV acceleration signal. Accordingly, the systolic optimization metric provided as input at block 432 may be derived from any cardiac signal available for evaluating cardiac systolic. Alternatively, the diastolic optimization metric provided as input at block 437 may be derived from any cardiac signal available for evaluating cardiac diastolic function.

The AV delay may be programmed to the optimal value at step 444. In some embodiments, prior to programming the AV delay to the optimal value, method 400 may determine at step 440 whether the optimal AV delay results in a clinically significant improvement in the optimization metric. If optimization of the timing parameter does not result in a significant improvement in the optimization metric, method 400 may alter the operating mode of the device at step 442. For example, the pacing mode may be adjusted to either deliver a different pacing therapy or withhold the current pacing therapy to conserve device longevity when the pacing therapy is not providing significant improvement in the optimization metric. Alternatively, the operating mode may be adjusted to override the user-selected optimization metric and repeat the optimization method 400 using a different optimization metric by returning to step 410 after recognizing the new operating mode at step 445.

At step 445, method 400 determines if the AV delay needs to be optimized for different heart rates and/or a new operating mode such as a change in pacing therapy mode or optimization metric. Since the optimal AV delay may change for different heart rates and/or operating modes, It is recognized that different optimal AV delay settings may be determined for different heart rates and different operating modes. During an optimization procedure, the AV delay optimization may be repeated during different heart rates and/or different operating modes. The optimal AV delays found for different heart rates and/or operating modes may be stored such that the AV delay may be automatically adjusted as heart rate and/or operating mode changes.

Thus, a method and apparatus for optimizing pacing timing control parameters have been presented in the foregoing description with reference to specific embodiments. It is appreciated that various modifications to the referenced embodiments may be made without departing from the scope of the invention as set forth in the following claims.

The invention claimed is:

1. A method for use in an implantable medical device programmed to deliver a pacing pulse in response to a timing control parameter, comprising:
   storing a user-selected optimization metric;
   iteratively adjusting the timing control parameter;
   providing a pacing pulse to a ventricular heart chamber in response to the time control parameter;
   sensing a first signal that varies in response to left ventricular wall acceleration;
   measuring the user-selected optimization metric in response to the sensed first signal; and
   determining an optimal timing control parameter value in response to the measured user-selected optimization metric; and
   wherein measuring the user-selected optimization metric includes minimizing the effect of non-cardiac signal contributions to the first sensed signal.

2. A method according to claim 1 wherein measuring the user-selected optimization metric includes setting a first signal sensing window in response to the user-selected optimization metric.

3. A method according to claim 1 wherein measuring the optimization metric includes measuring one of: a first maximum peak, a second maximum peak, a first minimum peak, a second minimum peak, a slope, a morphological signature, a threshold crossing, an inflection point, and a temporal separation of the first maximum peak and the second maximum peak.

4. A method according to claim 1 wherein storing the user-selected optimization metric includes storing a user-selected cardiac cycle phase to be optimized.

5. A method according to claim 1 wherein measuring the user-selected optimization metric includes verifying a predetermined stability requirement.

6. A method according to claim 5 wherein the predetermined stability requirement includes at least one of: a heart rate, a pacing mode, a respiration rate, an activity level, a time of day, a posture.

7. A method according to claim 1 wherein minimizing the effect of non-cardiac signal contributions includes sensing a second signal that varies in response to non-cardiac motion.

8. A method according to claim 1 further including determining a heart rate and wherein measuring the user-selected optimization metric in response to the sensed first signal includes measuring the user-selected optimization metric at a plurality of heart rates and wherein determining the optimal timing control parameter value in response to the measured user-selected optimization metric includes determining the AV delay in response to the heart rate.

9. A method according to claim 1 further comprising:
   storing a second optimization metric;
   sensing a second signal that varies in response to cardiac function; and
   measuring the second optimization metric in response to the second signal, and wherein determining the optimal timing control parameter value includes determining the optimal timing control parameter value in response to the second optimization metric.

10. A method according to claim 9 wherein the second signal includes any of a left ventricle acceleration signal, a right ventricle acceleration signal, a pressure signal, an impedance signal, a flow signal, and a blood chemistry signal.

11. A method according to claim 1 wherein the timing control parameter includes an AV delay.

12. A method according to claim 1 further including:
   determining if the optimal timing control parameter value results in an improvement in the optimization metric, and
   responding to determining if the optimal timing control parameter value results in an improvement in the optimization metric wherein the response includes one of programming the timing control parameter to the optimal value in response to determining an improvement in the optimization metric and altering an operating mode of the implantable medical device in response to determining no improvement in the optimization metric.

13. A method according to claim 1 wherein storing the user-selected optimization metric includes storing a pacing mode.

14. A method according to claim 1 wherein storing the user-selected optimization metric includes storing a physiologic condition.

15. A method according to claim 14 wherein the physiologic condition is one of heart rate, metabolic activity, posture, and blood pressure.

16. A system for providing a cardiac stimulation therapy, comprising:
   a programmable memory for storing a user-selected optimization metric;
   an output circuit for providing a pacing stimulus to a ventricular heart chamber in response to a timing control parameter;
   a first transducer for sensing acceleration of a portion of a left ventricle and providing a first signal related to the acceleration;
   an input circuit for receiving the first transducer signal; and
   a processor for determining the user-selected optimization metric in response to the first transducer signal received by the input circuit and for determining an optimal timing control parameter value in response to the user-selected optimization metric; and further including means for minimizing the effect of non-cardiac acceleration signals on the first transducer signal.

17. A system according to claim 16 wherein the first transducer includes an accelerometer disposed along the left ventricular free wall.

18. A system according to claim 16 further including means for verifying a stability requirement.

19. A system according to claim 18 wherein the means for verifying the stability requirement includes any of an activity sensor, a clock, a posture sensor, a heart rate detector and a respiration rate detector.

20. A system according to claim 16 wherein the means for minimizing the effect of non-cardiac acceleration signals includes a second transducer adapted to be disposed at a non-cardiac location.

21. A system according to claim 16 further including a heart rate detector and wherein the processor determines the optimal timing control parameter value for a plurality of heart rates.

22. A system according to claim 16 further including a second transducer for sensing a second signal related to cardiac function and wherein the processor determines a second optimization metric in response to the second signal and determines the optimal timing control parameter value in response to the second optimization metric.

23. A system according to claim 16 wherein the timing control parameter includes an AV delay.

24. A system according to claim 16 further including:
means for determining if the optimal timing control parameter value results in an improvement in the optimization metric, and
means for responding to determining if the optimal timing control parameter value results in an improvement in the optimization metric wherein the response includes one of programming the timing control parameter to the optimal value in response to determining an improvement in the optimization metric and altering an operating mode of the implantable medical device in response to determining no improvement in the optimization metric.

25. A system according to claim 16 wherein storing the user-selected optimization metric includes storing a pacing mode.

26. A system according to claim 16 wherein storing the user-selected optimization metric includes storing a physiologic condition and further including means for determining the physiologic condition.

27. A system according to claim 26 wherein the physiologic condition is one of heart rate, metabolic activity, posture, and blood pressure.

* * * * *

UNITED STATES PATENT AND TRADEMARK OFFICE
CERTIFICATE OF CORRECTION

PATENT NO.      : 7,653,437 B2
APPLICATION NO. : 11/344471
DATED           : January 26, 2010
INVENTOR(S)     : Prakash et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1017 days.

Signed and Sealed this

Twenty-third Day of November, 2010

David J. Kappos
*Director of the United States Patent and Trademark Office*